United States Patent [19]

McDevitt

[11] 4,237,734
[45] Dec. 9, 1980

[54] DEVICE FOR OBTAINING A SAMPLE OF LIQUID

[76] Inventor: Robert F. McDevitt, Box 551 Ogden Dunes, Portage, Ind. 46368

[21] Appl. No.: 29,985

[22] Filed: Apr. 16, 1979

Related U.S. Application Data

[60] Continuation-in-part of Ser. No. 907,109, May 18, 1978, abandoned, which is a division of Ser. No. 720,697, Sep. 7, 1976, Pat. No. 4,112,772, which is a continuation of Ser. No. 565,396, Apr. 7, 1975, abandoned.

[51] Int. Cl.³ .............................................. G01N 1/12
[52] U.S. Cl. ............................................ 73/425.4 R
[58] Field of Search .................... 73/425.4 R, DIG. 9

[56] References Cited

U.S. PATENT DOCUMENTS

| 387,174 | 7/1888 | McLean | 249/119 |
|---|---|---|---|
| 2,515,060 | 7/1950 | Smith | 73/DIG. 9 |
| 3,415,124 | 12/1968 | Collins | 73/425.4 R |
| 3,552,214 | 1/1971 | Collins | 73/425.4 R |
| 3,554,040 | 1/1971 | Collins | 73/425.4 R |
| 3,646,816 | 3/1972 | Hance | 73/425.4 R |
| 3,983,755 | 10/1976 | Collins | 73/425.4 R |
| 4,125,024 | 11/1978 | Vierbicky | 73/425.4 R |
| 4,137,774 | 2/1979 | Kumbrant | 73/425.4 R |

FOREIGN PATENT DOCUMENTS 2218022 9/1974 France .............................. 73/425.4 R

*Primary Examiner*—S. Clement Swisher
*Attorney, Agent, or Firm*—Charles S. Penfold

[57] ABSTRACT

A mounting which serves the dual purpose of supporting a device having a chamber for receiving a sample of molten material and connecting the device to a front end of a lance or wand whereby to facilitate manipulation of the device into a supply of such a material. The device also embodies improvements with respect to the flow of the material into the device and its structure which is adapted to engage the mounting whereby to support the device in a stable axial relation to the mounting. Additional improvements reside in providing a first hollow member which is operatively connected to the mounting for protecting a tubular entrance leading to the chamber, a second hollow member attached to the first member for protecting the latter, and means carried by one or both of the members whereby to control the inflow of the material and condition the same prior to its entry into the chamber.

43 Claims, 26 Drawing Figures

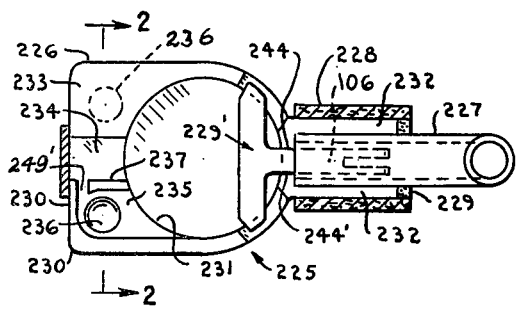
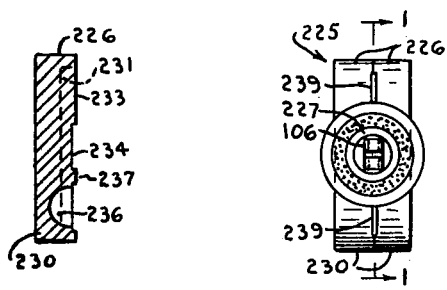
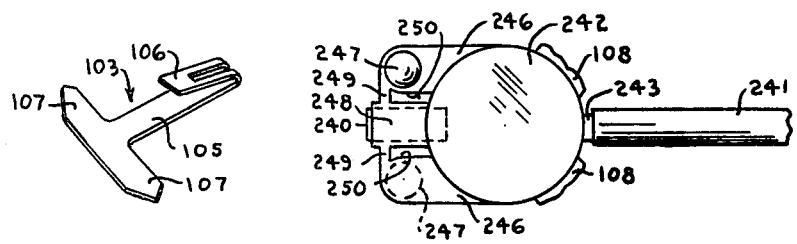
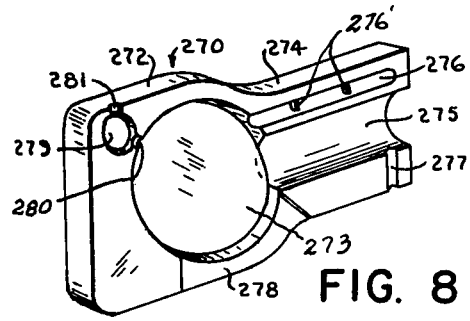
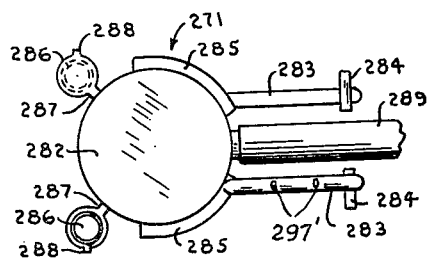
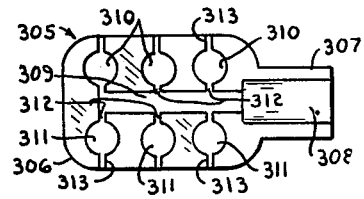
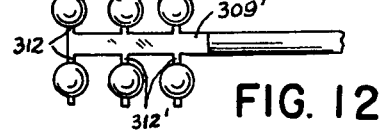

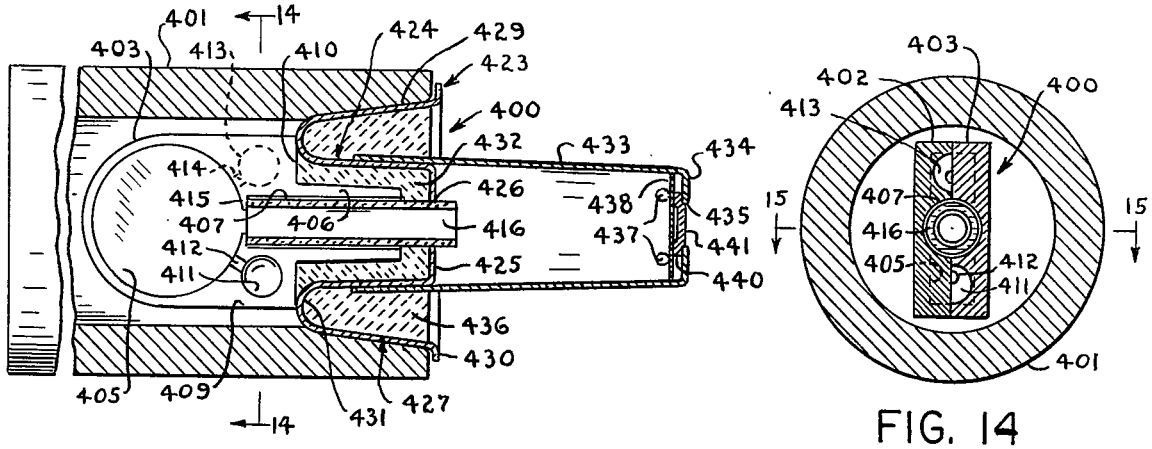
FIG. 13  FIG. 14
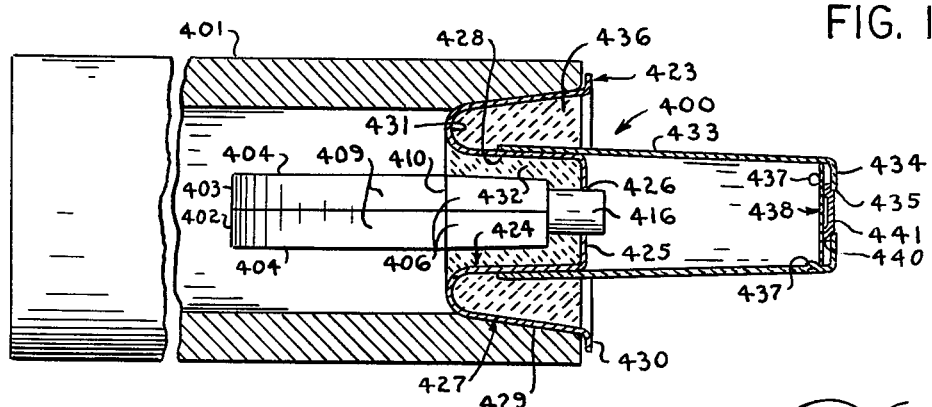
FIG. 15
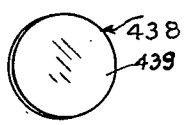
FIG. 19
FIG. 18
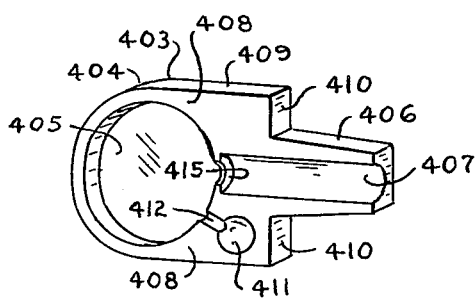
FIG. 17
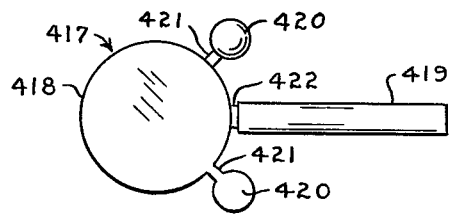
FIG. 16

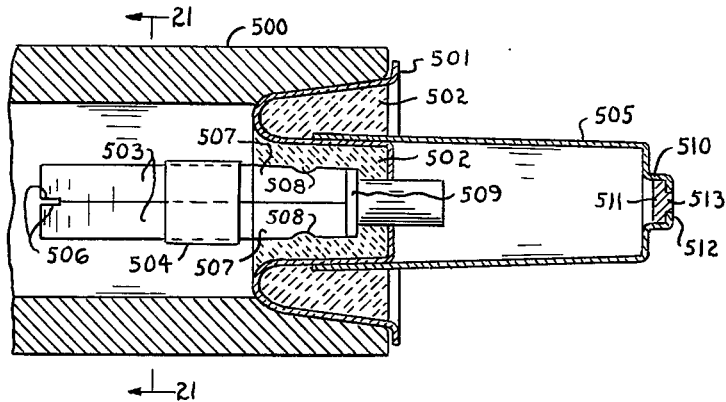
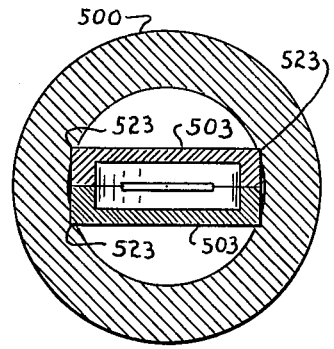
FIG. 20  FIG. 21
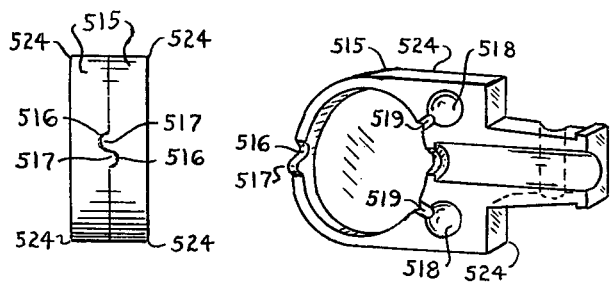
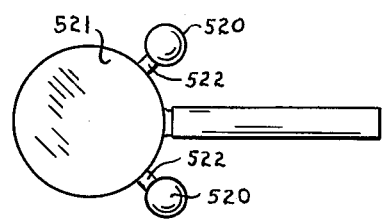
FIG. 23  FIG. 22  FIG. 24
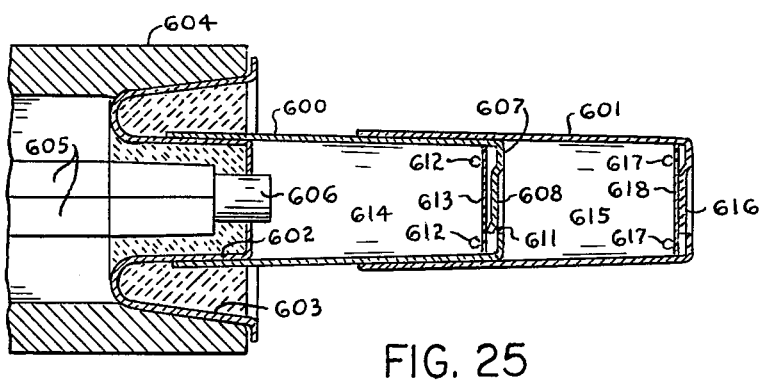
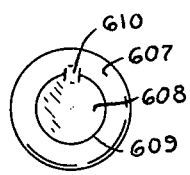
FIG. 25  FIG. 26

DEVICE FOR OBTAINING A SAMPLE OF LIQUID

This application is a continuation-in-part of application Ser. No. 907,109, now abandoned, which is a Division of application Ser. No. 720,697 filed Sept. 7, 1976, now U.S. Pat. No. 4,112,772 and the latter is a Continuation of my application Ser. No. 565,396 filed Apr. 7, 1975, now abandoned.

The invention involves various forms of devices and methods for obtaining various forms of samples of molten metal, and various forms of connectors attachable to a lance for detachably connecting the devices thereto.

More particularly, the purpose of the invention is to provide a safe and simple method whereby a cast sample for example, may be obtained from a flowing metal stream when molten metal is being transferred by pouring from one type vessell to another. The cast sample may consist of a disc with one or more smaller cast extensions attached to the disc. The size and shape of the casting is designed to provide a precision sample, requiring a minimum of preparation, that meets laboratory testing procedures. The disc may be used directly for spectographic analysis or can be drilled to provide a sample for wet chemical analysis. In addition, the sample may be sawed and polished for use in metallographic study of grain structure, cleanliness, etc. The smaller cast extensions are of precision dimensions with indexed separation points to permit detaching a sample of precise weight, minimizing preparation. These smaller samples are suited for analysis of such elements as sulfur or carbon.

The entire sample (disc and extension) can be cast in a piece mold assembly made of a material with optimum cooling venting and dimensional characteristics. This sample is representative of the material being tested and can be used for either chemical analysis or metallographic examinations.

DESCRIPTION OF THE TESTING PROCEDURE

In the processing of metals in the molten state it is necessary to obtain a sample representative of the parent material, at various stages in the processing, for the evaluation of either its chemical composition or metallographic structure.

The device or sampler embodying the subject invention is preferably designed to obtain a quick chilled sample from the flowing metal as it is transferred by pouring from one type vessel to another. It is primarily designed to be used where molten steel is poured from a teeming ladle into a mold. The molten steel is teemed through a nozzle in the bottom of the ladle, and the resulting stream is controlled through use of a mechanical, electro, or hydraulic valve arrangement. The diameter of the stream can be from $\frac{3}{4}''$ to $3\frac{1}{2}$ depending on the rate of flow desired.

The device also has application in the continuous casting process during transfer of molten metal from ladle to tundish to mold under controlled condition. This device has further application in any area or with any molten metal where the molten metal is transferred from one vessel to another under controlled conditions.

For many years the typical method of sampling molten metal in the steel industry was to use what was defined as a spoon. The spoon consisted of a deep bowl type ladle or sampler attached to the end of a long handle and made of either cast or forged steel. The spoon varied in size and had a lip to facilitate pouring.

In practice the pouring stream was controlled to a slow or partial stream and the spoon was then dipped into the stream of metal to obtain the sample. The spoon was usually tipped into either the right or left side of the stream, whichever was most convenient, and partially filled with molten metal. The molten metal content of the spoon was then poured into a small test mold positioned on the platform. The casting from this mold provided a sample 4" to 8" long, tapered, and 1" to 2" square in cross-section. The sample could be sawed or drilled in the laboratory to provide samples for wet chemistry analysis, spectographic analysis or metallographic evaluations. The samples obtained as described above are used to represent a portion of the metal in the teeming ladle at given intervals in the pouring process.

This conventional method of sampling is not only wasteful from the standpoint of time and material but also exposes the molten metal to atmospheric oxygen which can cause variations in the chemical content of the sample. The degree of the chemical variation is dependent on the grade of steel as well as the techniques of the individual doing the sampling. The effect is most pronounced with the elements of carbon and manganese with varying effects on other elements. Although the steel industry has been aware of the phenomenon and does make corrections; much could be gained by minimizing this condition. Other disadvantages of this conventional method are the need to arrest the stream and the extreme safety hazards involved with taking a sample when the molten metal stream cannot be controlled.

Advantages of the invention or inventions over the spoon technique are:

1. Minimum exposure of the sample to atmospheric oxygen.
2. Simplified sampling technique eliminating the heavy spoon and repouring technique.
3. Elimination of the need to arrest the molten metal stream flow.
4. Precision cast samples with a quick chill and tailored for minimum preparation.
5. Representative and reproducible results at a minimum of expense.
6. Safe procedure in obtaining samples.

In view of the foregoing, one of the important objects of the invention is to provide an elongated device for obtaining a sample of a liquid, such as molten metal, which comprises, among other things, a pair of half sections forming a chamber, tubular means which has an inner extremity communicatively connected to the chamber and an outer extremity provided with an entrance for initially receiving molten metal for flow into the chamber, means at one extremity of the device for holding the sections together, and means at its opposite extremity for holding the sections and tubular means assembled, and wherein one or both of these holding means may serve to facilitate disassembly of the sections. More particularly in this respect, one of the holding means for the sections comprises clip means, and an appendage held in place by this clip means may be utilized for identificating purposes and effect release of the clip means, and the means for holding the sections and tubular means may be operated to facilitate disassembly of these components.

A significant object of the invention is to provide a device of the character described above in which each section includes a relatively large head portion provided with a recess and an extended portion having a center groove therein so that when the sections are correctly assembled the recesses will form a primary chamber and the grooved extensions will form a tubular formation communicating with the chamber.

Also, an object of the invention is to provide a device as described in the preceding paragraph in which the head portions of the sections are also provided with recesses which form additional secondary chambers which receive molten metal from the primary chamber.

A specific object is to provide a device in which the head portions form a plurality of rows of chambers for receiving molten metal.

Also, an object is to provide a device whereby different forms of sample portions may be obtained. More particularly, one sample may include a large head or stem, and longitudinal and offset portions joined to the head, and others in lieu of a large head include a plurality of relatively small joined round portions or joined parallel portions.

Further objects of the subject invention reside in providing unique means for supporting extensions of a pair of mating half mold sections in a central mass of insulating material carried by a mounting or support; providing an elongated forwardly extending hollow member or support which is connected to the mounting and serves to protect a tubular entrance leading to a chamber formed by the sections; and an outer annular mass of insulation material which is carried by the mounting and assists in holding the hollow member in relation to the mounting.

A specific objective is to provide the hollow member with a front opening, internal abutment means, means for conditioning molten material disposed in relation to the abutment means, and a closure interposed between the conditioning means and opening for normally closing the latter.

Also the invention contemplates providing means on the channel portions of the sections whereby to assist in holding them together in a mass of cement; providing means on the sections for biting into or intimately engaging on outer housing whereby to assist in holding the sections in the housing; means on the head portions of the sections whereby to assist in locking them together; providing a vent for the primary chamber formed by the head portions; providing the sections with recesses which cooperate to form a pair of spherical sample portions; and in providing a modified form of hollow member at the front of the device and which serves as a mixing chamber for molten material and means for conditioning the material.

A further object is to provide a modified form of an assembly for attachment to a mounting whereby a pair of mixing chambers and a pair of conditioning means and a pair of closure means can be utilized with respect to an inflow of material to be sampled.

Additional objects and advantages of the invention reside in providing a device which is safe and efficient to use, durable and comprised of components which can be economically manufactured and assembled on a production basis.

Other objects and advantages will become apparent after the description hereinafter set forth is considered in conjunction with the drawings annexed hereto.

DRAWINGS

In the drawings:

FIG. 1 is a longitudinal section taken substantially on line 1—1 of FIG. 3 of a device;

FIG. 2 is a transverse section taken substantially on line 1 of FIG. 1;

FIG. 3 is one end view of the device of FIG. 1;

FIG. 4 is a perspective view of a deoxidizing element which may be utilized in conjunction with the device shown in FIG. 1;

FIG. 5 is a top view of sample of molten metal obtained by using the device shown in FIG. 1;

FIG. 6 is a side view of the sample shown in FIG. 5;

FIG. 7 is one end view of the sample depicted in FIGS. 5 and 6;

FIG. 8 is a perspective view of one of a pair of half sections of a modified device;

FIG. 9 is a face view of a sample obtained by using the device shown in FIG. 8;

FIG. 10 is an end view of the sample shown in FIG. 9;

FIG. 11 is an inside view of one of a pair of half sections of a modified device;

FIG. 12 is a sample obtained by utilizing a pair of half sections of the shape shown in FIG. 11;

FIGS. 13 through 26 are directed to structures added to that disclosed in the Divisional application Ser. No. 907,109;

FIG. 13 is a partial section of structure comprising an outer tubular housing and a device secured in a front extremity of the housing for using samples of molten material;

FIG. 14 is a transverse section taken substantially on line 14—14 of FIG. 13;

FIG. 15 is a transverse section taken substantially on line 15—15 of FIG. 14;

FIG. 16 is fore view of a composite sample structure obtainable by the device;

FIG. 17 is a perspective view of one of the half mold sections;

FIG. 18 is a pictorial view of a means which may be utilized to condition the molten material as it flows into a chamber formed by the mold sections;

FIG. 19 is a pictorial view of a closure or member for normally closing an opening provided in the forwardly extending hollow member above referred to;

FIG. 20 is a modified structure;

FIG. 21 is a transverse section taken on line 21—21 of FIG. 20;

FIG. 22 is a modified section of a pair for use in a device for obtaining a sample of molten material;

FIG. 23 is an end view of a pair of the sections of FIG. 22;

FIG. 24 is a view of a sample, similar to FIG. 16, on which a pair of relatively small spherical portions are obtained;

FIG. 25 illustrates a modified structure for use with a device; and

FIG. 26 is an end view of one of the hollow members of FIG. 25 showing a portion which is partially severed from an end wall of the member.

FIGS. 1, 2 and 3 disclose a device generally designated 225 whereby a sample or portions may be obtained as shown in FIGS. 5, 6 and 7 and one or more portions thereof may be removed. The device 225 is substantially the same as the device 90 depicted in application Ser. No. 720,697 except that it includes half sections generally designated 226 which embody different and unique structural advantages. The device does include a tubular means 227, sleeve 228, washer or cement 229 and the deoxidizing element 229' like 103 in said application Ser. No. 720,697.

As to the half sections 226, each comprises a generally rectangular head portion 230 provided with a round recess 231, channel portions 232 (one shown) and a solid outer end portion 233 provided with an axially extending rectangular slot 234, a relatively shallow recess 235 which is provided with a substantially semispherical secondary chamber or pocket 236, a longitudinally extending rib 237 constituting a side wall of the slot 234. When the sections are correctly assembled, the recesses 231 define: a primary chamber for receiving molten metal from the tubular means 227, the side notches, openings or vents 239 for the portions of the deoxidizing element 229', the axial slots 234 an opening which receives a portion of an appendage 240, as shown in FIG. 5; the shallow recesses 235 on the opposite sides of the longitudinal axis of the device respectively provide relatively broad passages through which metal may flow into the opening formed by the axial notches 234. Otherwise expressed, metal may flow from the primary chamber into the secondary chambers 236 and vents 239 so that when the metal solidifies a sample or portions will be obtained as shown in FIGS. 5, 6 and 7. An appendage 240, like the appendage 241' in said application Ser. No. 720,697 is preferably disposed in the axial opening for imbedment in metal and clip means is also employed for detachably holding head portions of the sections together. The size of the secondary chambers 236 are preferably predetermined so that, for example, portions obtained will each weigh one gram. However, it is to be understood that these secondary chambers may be in different sizes and shapes.

The deoxidizing element 229' corresponds to the element 103 in FIG. 4 and is preferably T-shaped or articulated and includes a stem 105 having a slotted continuation 106 bent back at an acute angle over the stem and a pair of opposed portions 107 constituting the cross of the T. This element is secured in place by locating remote ends of the portions 107 in the vents and the stem 105 and its continuation 106 in the tubular means 99 as shown in said application Ser. No. 720,697 so as to insure the inflow of metal will be thoroughly subjected to conditioning by the deoxidizing means both in the tubular means and chamber. The continuation 106 due to its slotted character serves to expedite melting thereof and conditioning of the metal. The free ends of the portions 107 of the element are preferably bevelled or pointed to some extent as shown in FIGS. 1 and 4 for disposition in side openings or vents 96 formed by the notches in the head portions so that some metal may flow outwardly through the vents to provide laterally extending arcuate portions 108 of a sample as depicted in FIG. 5, which will be described subsequently with respect to the device exemplified in FIGS. 1, 2 and 3.

More particularly, the sample or portions illustrated in FIGS. 5, 6 and 7 include a cylindrical stem portion 241 formed in the tubular means 227, a round head portion 242 of substantially uniform thickness which may correspond to the cross-dimension of the stem portion and an intermediate restricted portion 243 formed in a passage 244 of the sections. The material defining the passage constitutes an abutment 244'. Attached to the head 242 are circumferentially spaced relatively thin outwardly extending radial portions 108 formed in the side openings or vents 239, a pair of parallel relatively thin portions 246 of uniform thickness which are located on opposite sides of and in parallel relation to the longitudinal axis of the stem. The portion 246 are formed in the recesses 235 and extend in a direction opposite to that of the stem and the outer extremity of each of the portions 246 includes hemispherical portions 247 formed in the secondary chambers 236, each of which is intended to weigh, for example, one gram. It will be noted an axially extending portion 248 is formed in the opening formed by the slots 234 and that the portion 248 is joined to the outer extremities of the parallel portions 246 by portions 249 formed in passages 249'. It should also be noted that the head portion, parallel portions, axial portion and transverse portions define openings 250.

FIG. 8 is a perspective view of a modified form generally designated 270 of one of a pair of half sections which in combination with a tubular means, and a sleeve corresponding to those shown in FIG. 1, serve to obtain a sample generally designated 271 as exemplified in FIGS. 33 and 34 in said application Ser. No. 720,697.

Attention is directed to the fact that the portions 283, 284, 287 and 288 are substantially semi-circular in cross-section and this is due to the fact that each of the grooves in each half section forming such portions cooperate with a planar portion of the other half section. For example, the longitudinal groove 276 of half section 270 is covered by an abutting planar portion of an extended portion like 274 of a mating half section (not shown). Attention is also directed to the fact that except for the center groove 275 and round recesses 273 of the sections, all of the other grooves and smaller recesses define what may be termed a plurality of secondary chambers or cavities which receive molten metal for analysis in addition to the head and stem portion of the sample. The small truncated sample portions 286 obtained preferably have a weight of substantially one gram when severed from the head portion for analysis. It should be noted that the portions 286 are joined to the head portion by the portions 287 which are relatively thin whereby to facilitate severance of the portions and the portions 283 can also be readily severed from the head portion since they too are joined to the head by the portions 285 which are relatively thin in cross-section.

Attention is also directed to the important fact that the projections or markers 276' serve to selectively divide and measure each of the longitudinal grooves 276 into three equal areas or zones as evidenced by the resulting notches or marking 297' of the samples shown in FIG. 9. Each of the sample portions 283 thereby comprise three portions which may be readily separated at the notches to obtain for example, three separate samples, each weighing one (1) gram for analysis.

FIG. 11 depicts an inner side view of a modified form generally designated 305 of one of a pair of half sections. Each section includes a head portion 306 and an extended portion 307 having a groove 308 therein. Each head is provided with an axially extending center groove 309, a row of three separate cavities 310 on one side of the center groove and a row or bank of three corresponding cavities 311 disposed on the other side of the center groove and in parallel relation with respect thereto. The cavities are communicatively connected with the center groove 309 by slots 312 and to the atmosphere through slots 313.

When the sections are correctly assembled with other components to complete a device the grooves 308 define a tubular formation for receiving a tubular means through which the molten metal flows to the cavities. The center grooves 309 define a center or primary chamber and the cavities 310 and 311 define secondary chambers for receiving molten metal from the center chamber and the passages 313 form vents to facilitate entry of the molten metal into the center and secondary chambers. The center grooves and cavities are preferably semi-circular in cross-section but if so desired, one of the sections may be provided with a planar inner face side for covering the grooves and cavities in the other section, in which event, the sample portions formed by the center groove and those formed in the cavities will be semi-circular in cross-section in lieu of being circular in cross-section. This organization affords a setup whereby multi-portions of samples of corresponding predetermined sizes or weights may be readily obtained for analysis.

More specifically, FIG. 12 shows a sample obtained by using a pair of assembled half sections 305. The center groove or grooves 309 for a sample portion 309' joined to a stem and portions 311' are formed in the cavities 310 and 311 and are joined to the center sample portion 309' by connecting portions 312' formed in the slots 312. Obviously, the portions 312' may serve to facilitate severance of the portions 311' for analysis.

It is understood that the half sections or receiving means can be fabricated from any material initially for the purpose, such as ceramic material, solid cast or forged metals such as copper, iron and steel, stamped from sheet metal stock. Sintered powdered metal is preferred because of certain unique characteristics it possesses. A properly designed powdered metal mold with adequate venting will form a fast chilled sample with a minimum of chemical segregation, optimum metalographic structure and precision dimensions for ease of preparation and analysis.

It is to be further understood that certain FIGURES of the drawing and descriptions with respect thereto are presented for the purpose of providing information and a foundation for the structure shown in FIGS. 11 and 12.

Elucidating further with respect to the use of the device in obtaining a sample, the sampling device is attached to the end of the lance or wand 4 as shown in application Ser. No. 720,697 so that the feed tube of the device is perpendicular to the axis of the pole. The individual taking the sample grasps the handle, faces the stream of molten metal, and holding the sample such that the feed tube of the device is near and parallel to the flow of the metal stream, twists the assembly so the open end of the feed tube is injected into the flow of the molten metal. The opening of the tube should be held at an angle to permit an unrestricted flow of the metal down the inside of the tube into the interior of the device. The open end of the tube is inserted just inside the outer surface of the stream to utilize the full volumetric capacity of the feed tube and minimize exposure of the incoming metal to the atmosphere.

As the sampling time using the invention so short, the sample size small and the mold enclosed, exposure to the atmosphere is greatly reduced, therefore reaction of the molten metal with oxygen is limited. Another important factor is the rapid transformation is accelerated by the mold design and the material employed. Rapid solidification minimizes chemical segregation and promotes a uniform structure.

It is theorized that when a molten metal sample is taken using powdered metal molds the sample is transformed quickly from the liquid to solid state by the combined action of the emissivity of the surface which allows the sintered iron mold to absorb the heat rapidly and the good conductivity of the iron allows the heat to transfer throughout the mass of the mold by conduction and convection. The good radiation characteristics of the outer surface allows for dissipation of the heat to the atmosphere. The quick chill effect of the mold design of the device coupled with its venting characteristics have permitted the design to incorporate the use of small extensions attached to the primary disc. These extensions are used primarily for the analysis of carbon and sulfur and their globular shape allows uniform cooling and solidification of the molten metal with a minimum of chemical segregation. Analysis of the elements from these samples may compare more favorably with analysis of drillings obtained from the primary disc and also with analysis obtained from product checks and possibly samples severed from glass enclosed pine which may cool differentially and have a tendency to segregate chemically.

Referring to the structure disclosed in FIGS. 13 through 19, there is depicted a device generally designated 400 which is secured in the front extremity of an elongated outer tubular housing 401 of pasteboard, the latter having a rear opening for receiving a lance for supporting the device whereby to facilitate manipulation of the device into a supply of molten material for obtaining samples therefrom.

The device 400 may be designed and constructed in various ways and as shown in FIGS. 13, 15 and 17, it preferably includes a receiving means comprised of a pair of mating half mold sections 402 and 403, each of which is provided with a head portion 404 having a large round recess 405 and a smaller or reduced extension 406 having a semi-cylindrical longitudinal groove 407 therein. Each of the sections is preferably relatively enlarged throughout the major portion of its length so as to form intermediate side portions 408 having parallel edge surfaces 409 and shoulder portions 410 as best illustrated in FIGS. 13 and 17.

One of the side portions 408 of section 403 is preferably provided with a small round concave cavity 411 which is communicatively connected to the recess 405 by a relatively small semi-cylindrical longitudinal groove 412 and a side portion of section 402 is provided with a cavity 413 and a groove 414 similar to the cavity 411 and groove 412 in section 403. Each of the sections is also provided with an internal notched abutment 415 at the inner end of each of the grooves 407.

When the sections are correctly assembled as depicted, the recesses 405 form a primary chamber for receiving molten material and the grooves 407 and extensions 406 form a tubular formation which serves to receive the inner extremity of a non-metallic tubular means or member 416 or entrance through which the material will flow into the primary chamber. The forward or outer extremity of the member is extended beyond the outer end of the tubular formation and its inner end is disposed to engage the abutments 415, the notches in the latter forming an inlet connecting the interior of the member 416 and chamber.

The organization is also preferably such that the cavity 411 in section 403 in combination with an opposed planer inner surface of section 402 serves to provide a secondary chamber and the cavity 413 in section 402 in combination with an inner planer surface of section 403 also provides a secondary chamber so that when molten material flows into the primary chamber some of the material will also flow into the secondary chambers formed by the cavities 411 and 413, through passages formed by the grooves 412 and 414 whereby to obtain the sample structure 417 as exemplified in FIG. 16. This sample structure includes a relatively large circular portion 418 of substantially uniform thickness, an elongated cylindrical stem portion 419, a pair of semi-spherical portions 420, the latter of which are joined to the large portion 418 by intermediate restricted portions 421 and a neck portion 422 joining the portions 418 and 419.

Attention is directed to the fact that the secondary chambers are preferably located intermediate the length of the device, on opposite sides of the longitudinal axis of the tubular formation and that the passages formed by the small grooves 412 and 413 are disposed at oblique angles with reference to this axis so that there is what may be termed a generally back or reverse flow of the material, as distinguished from a through or rear flow as shown in FIG. 1.

The device 400 is mounted in a unique way in the outer housing 401 and this comprises the use of a mounting or support generally designated 423 having a central hollow formation generally designated 424 which tapers forwardly and has an end wall 425 provided with an aperture 426 through which the tubular member 416 extends.

The mounting 423 also includes an outer annular formation generally designated 427 which tapers rearwardly, a wall 428 of the mounting being common to the formations 424 and 427. The center formation 424 is substantially disposed within the confines of the mounting and the outer formation 427 has an outer wall 429 provided with an outwardly extending radial flange 430. The walls 428 and 429 are joined by an inner curved wall 431.

The reduced extensions 406 are disposed in the central formation 424 and preferably held assembled and in this formation by a mass of insulating material or cement 432 which surrounds the extensions and a portion of the tubular means 416 as clearly shown in FIG. 15.

The device and mounting when assembled constitute a unit which is preferably secured in the front extremity of the outer housing by press fitting the unit into place to compress an inner portion of the housing and so that the radial flange 430 is either disposed in relation to or engages the end of the housing for protecting the same. It will be noted that the front extremity of the tubular means 416 extends a relatively short distance in advance of the front end of the housing.

The structure may be provided with an elongated frusto-conical metal casing 433 having a front end wall 434 having an opening 435 therein. The inner extremity of the casing may be connected to the mounting 423 in various ways but is preferably attached to the center formation 424 by press fitting the casing onto this formation so that the major portion of the casing extends forwardly of the formation in protective relation to the fore end of the tubular means 416. The annular formation 427 is preferably filled with a mass of insulating material or cement 436 which surrounds an inner portion of the casing whereby to assist in holding the casing connected to the mounting. The opening 435 in the front end wall 434 initially receives molten material for flow into the casing. The front extremity of the casing is provided with internal abutment means 437 which is in the form of circumferentially spaced inwardly extending projections as shown or the abutment means may be in the form of a circular internal rib. Means 438, preferably in the form of a meltable disc or element 439 is disposed in the casing against the abutment means 437 for conditioning the molten material as it flows into the casing. The opening 435 in the front wall of the casing is preferably closed by a meltable closure or disc 440 which is held between the abutment means 437 and end wall 434 and has a center projection 441 which extends into the opening 435 for normally closing the latter whereby to initially prevent entry of molten material in the casing when the device is initially inserted into a supply of molten material for obtaining a sample therefrom. Insertion of the device into the molten material causes the closure to melt to allow entry of some material for flow against the means 438 causing it to melt and mix with the material within the confines of the casing for conditioning the material prior to its flow into the primary and secondary chambers. The element 439 is preferably constructed of aluminum but other material suitable for the purpose may be utilized depending in some instances on the character of the molten material to be sampled.

The structure illustrated in FIG. 20 is similar to that of FIG. 13 and comprises an outer housing 500, a mounting 501 containing masses 502 of cement, a pair of mating sections 503 which are preferably held together by a flexible means, such as a band of tape 504, and a front casing or hollow member 505.

The sections have head portions which are provided with rear corresponding mating notches 506 which cooperate to form a vent for the primary chamber formed by the recessed head portions. The sections also have channel portions 507 and each of these is preferably provided with an indent or recess 508 and a lateral projection 509 constituting means which respectively receive and project unto the mass of cement whereby to assist in holding the sections to the cement.

The casing or hollow member 505 is provided with a relatively small forwardly extending protuberance 510 forming a recess in which an element 511 for conditioning the molten material is secured. The front wall of the protuberance is provided with an opening 512 and the element 511 has a projection 513 which extends into this opening for normally closing it. This element is preferably press-fitted into place or the protuberance may be deformed to hold the element in place.

In FIG. 23 there is shown a pair of sections 515 having head portions having rear rims provided with adjacent notches 516 and projections 517 which cooperate to interlock the head portions or sections and each of the sections is also provided with a pair of relatively small concave recesses 518, as shown in FIG. 22, which are connected to a primary chamber by semi-cylindrical narrow grooves 519. The arrangement is such that when the sections are correctly assembled in a device, the recesses 518 and the grooves 519 will respectively form substantially round secondary chambers and cylindrical passages which serve to receive molten material whereby to form a pair of spherical sample portions 520 joined to a large head portion 521 by a pair of reduced cylindrical portions 522 as shown in FIG. 24.

Attention is directed to the fact that the major portion of each of the sections 503 is generally rectangular in shape and that these sections, due to the planar external surfaces provide a plurality of longitudinally extending sharp edges or arrises 523 which bite into or intimately engage the interior of the housing 500 as depicted in FIG. 21 whereby to maintain the sections assembled with respect to one another and the housing when the sections are press fitted into place. The sections 515 of FIGS. 22 and 23 are similarly provided with edges or arrises 524.

It should be noted that the channel portions 406 of FIGS. 13 and 15 and those of FIGS. 17, 20 and 22 are preferably tapered whereby to facilitate separation of the sections from the mass of cement after a sample has been obtained.

A modified structure is disclosed in FIGS. 25 and 26 for use with a device for obtaining a sample of molten liquid or material.

More particularly, this structure includes an inner metal hollow member or casing 600 and an outer metal hollow member or casing 601, which members are preferably tapered and telescopically connected by a press fit. The inner member is preferably press-fitted onto a tapered portion 602 of a mounting 603 which is secured to an outer housing 604. The mounting carries a pair of mating sections 605 which form a primary chamber and one or more secondary chambers for receiving samples of a molten material which flows into the chambers through a tubular means or entrance 606.

The front extremity of the inner member 600 has a front end wall 607 of which a center round portion 608 is partially severed at 609 to leave a connecting portion or hinge 610 which can be bent or flexed so that a tip of the center portion will provide a small opening as indicated at 611. This inner member is also provided with a plurality of dimples or projections 612 which constitute abutment means or seat means for a conditioning means or element 613 preferably in the form of a disc of aluminum which is interposed between the abutment means and the center portion 608 of the end wall 607 of member 600.

The inner member 600 in combination with the mounting 603 forms an inner mixing chamber 614 and the outer member 601 in combination with the inner member 600 forms or defines a front mixing chamber 615.

The outer hollow member or casing 601 has an end wall provided with a center portion 616 substantially the same as the portion 608 of member 600 and member 601 is also provided with suitable abutment means 617 and an element 618.

The setup is preferably such that when the device is utilized to obtain a sample of molten material the material will melt or cause the center portion 616 of the member 601 to move or pivot inwardly and thereby open the members and allow the material to also melt the element 618, preferably of aluminum, for mixing with the material to deoxidize it in the chamber 615, from whence the deoxidized material flows into the inner chamber 614 through an opening formed by the melting, deformation or movement of the center portion 608 and melting of element 613 to additionally deoxidize the material a second time prior to its flow into the tubular means or entrance 606.

It is to be understood that one or both of the hollow members 600 and 601 may be utilized; that if so desired only one may be provided with a deoxidizing element; and that the center portion 608 of member 600 may be eliminated, as well as element 613. The center portions 608 and 616 may be considered to constitute closures which are responsive to the molten material for opening up the hollow members for reception of the material. The hollow members are interchangeable and offer one or a pair of chambers in which the material can be conditioned prior to its flow into the entrance leading to one or more chambers formed by the mating sections of the device.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. A subassembly of a device for obtaining a sample of liquid from a supply thereof, said assembly being elongated and comprising wall structure forming a head and a reduced tubular extension, said head being provided with a row of separate chambers disposed alongside the longitudinal axis of said subassembly, said extension being provided with an opening, a longitudinal axial passage common to and establishing communication between said chambers and opening, and vents respectively provided for said chambers.

2. A sample of molten metal comprising a stem having a predetermined cross-dimension and a longitudinal portion of a lesser cross-dimension joined to said stem and constituting an integral continuation thereof, a row of aligned spaced portions disposed along one side of said longitudinal portion, and portions respectively connecting said spaced portions to said longitudinal portion whereby to facilitate severance of said connecting portions therefrom.

3. The sample defined in claim 2, including a second row of aligned spaced portions similarly connected to said longitudinal portion.

4. A subassembly of a device for obtaining a sample of molten material, said subassembly comprising a pair of sections, each of said sections having a rear head and a front reduced channel portion, said head of one of said sections being provided with a center recess, a small cavity located in close proximity to one of said channel portions and with a small groove connecting said recess and said cavity, and means for holding said sections assembled whereby said recesses, said cavities, said small grooves and channel portions respectively form a primary chamber, a secondary chamber, a passage communicatively connecting said chambers and a tubular formation for accommodating an inner extremity of a non-metallic tube through which the material may be caused to flow into said chambers.

5. The subassembly defined in claim 4, including a non-metallic tube having an inner extremity secured in said tubular formation and an outer extremity for initially receiving the material.

6. A subassembly of a device for obtaining a sample of molten material, said subassembly comprising a pair of sections, each of said sections having a rear head and a front reduced channel portion, said head of at least one of said sections being provided with a center recess, a small cavity located in close proximity to one of said channel portions and with a small groove connecting said recess and said cavity, and means for holding said sections assembled whereby said recess, said cavity, said groove and channel portions respectively form a primary chamber, a secondary chamber, a passage communicatively connecting said chambers and a tubular formation for accommodating an inner extremity of a non-metallic tube through which such a material may be caused to flow into said chambers.

7. The subassembly defined in claim 6, in which said passage is disposed at an oblique angle with respect to the longitudinal axis of said tubular formation.

8. A subassembly of a device for obtaining a sample of molten material, said subassembly comprising a pair of sections, each of said sections having a rear head and a front reduced channel portion, at least one of said sections having a center recess in its head and a small cavity located in close proximity to its channel portion and with a small groove connecting said recess and said cavity, and means for holding said sections assembled whereby said recesses, said cavity, said small groove and channel portions respectively form a primary chamber, a secondary chamber, a passage communicatively connecting said chambers and a tubular formation for accommodating an inner extremity of a nonmetallic tube through which the material may be caused to flow into said chambers.

9. A subassembly of a device for obtaining a sample of molten material, said subassembly comprising a pair of mating sections, at least one of said sections having a rear head provided with a center recess and a front reduced channel portion, said head also being provided with a small cavity located in close proximity to said channel portion and with a small groove connecting said recess and said cavity, and means for holding said sections assembled whereby said recess, said cavity, said groove and said channel portion in combination with the other section respectively form a primary chamber, a secondary chamber, a passage communicatively connecting said chambers and a tubular formation for accommodating an inner extremity of a non-metallic tube through which the material may be caused to flow into said chambers.

10. In combination: a one-piece mounting and a device having a chamber and a tubular entrance through which a hot liquid may be caused to flow into the chamber, said mounting comprising wall structure forming a central hollow formation having a front wall provided with an opening through which said tubular entrance extends and an outer wall substantially surrounding said formation, and a mass of insulating material disposed in said formation for surrounding at least a portion of said device for holding said mounting and device assembled to constitute a unit whereby said outer wall serves to facilitate attachment of this unit to a fore extremity of a support.

11. A subassembly for use in obtaining a sample of molten material from a supply thereof comprising a one-piece wall structure defining a central formation having an end wall provided with an aperture, means for receiving a sample having a portion disposed in said formation and provided with tubular means extending forwardly through said aperture for receiving the material for flow into said receiving means, a mass of insulating material disposed in said formation and surrounding at least a portion of said receiving means for holding said wall structure and receiving means assembled, said wall structure also including an outer wall substantially surrounding said formation and defining in combination therewith an external annular formation for reception in a front tubular extremity of an elongated outer housing.

12. The subassembly defined in claim 11, including a mass of insulating material secured in said annular formation in a substantially surrounding relation to said central formation.

13. The subassembly defined in claim 11, including a substantially hollow member having an inner end located in said annular formation and secured to said central formation serving to protect said tubular means, and means in said member disposed at a location forwardly of said tubular means for conditioning the molten material in said member prior to its flow into said receiving means via said tubular means.

14. The subassembly defined in claim 11, in which said receiving means has spaced portions engaging said central formation for locating said receiving means in axial relation to this formation and promoting stabilization.

15. The subassembly defined in claim 11, including an elongated support having a tubular front extremity in which said subassembly is secured, and said subassembly is provided with a hollow member which is secured to said central formation and extends forwardly of said extremity for protecting said central formation.

16. A subassembly for use with means for obtaining a sample of molten material comprising an elongated hollow member having a rear open extremity for attachment to a mounting and a front extremity provided with an end wall having an opening and an adjacent internal seat for means for conditioning such a material flowing into said member through said opening.

17. The subassembly defined in claim 16, including meltable means for conditioning the material normally preventing flow of such material through said opening.

18. A one-piece mounting for use with a device having a chamber and tubular means for receiving a sample of hot liquid for flow into the chamber, said mounting having a central hollow formation having a front wall provided with an opening for receiving such a tubular means and a rear open area for receiving a mass of insulating material for holding such a device in relation to the mounting and an outer wall substantially surrounding said formation for attachment to a tubular support.

19. A subassembly for use in protecting an entrance of a device having a chamber for obtaining a sample of molten material, said subassembly comprising wall structure forming a casing having a rear portion for connection with a part of the device for disposition about the entrance, and a front portion provided with internal abutment means assisting to support means for conditioning such a material substantially within the confines of the casing prior to its flow into such a chamber via the entrance.

20. The subassembly defined in claim 19, in which said front portion is provided with an opening for initially receiving such a material, and meltable means for normally closing said opening.

21. A hollow member for use in protecting the entrance of a device for obtaining a sample of molten material, said member having a front wall formed to provide a forwardly extending protuberance having an end wall provided with an opening, said protuberance forming a recess for receiving an element having a projection for disposition on said opening for normally closing the same.

22. The member defined in claim 21, including such an element secured in said recess.

23. A subassembly comprising a pair of mating sections having head portions forming a chamber for receiving a sample of molten material, and said head portions being provided with longitudinal extending arrises for engaging internal areas of an outer housing whereby to assist in holding the sections assembled with respect to one another and to such a housing.

24. A subassembly comprising mounting having a central hollow formation, a pair of mating sections forming a chamber for receiving a sample of molten material, said sections also forming a forwardly extending tubular formation, said tubular formation being provided with indents, and a mass of cement disposed in said hollow formation and said indents whereby to assist in holding the sections to said mass.

25. The subassembly defined in claim 24, including flexible means engaging said formation for holding said sections assembled.

26. A subassembly comprising a pair of mating sections having portions forming an enlargement providing a chamber and a tubular formation, said enlargement having rear rim portions, and said rim portions being respectively provided with contiguous recesses and projections which can be interengaged for interlocking said rim portions.

27. A member for the use described, said member being hollow and having a front extremity which is constructed to provide an integral pivotal portion which will be caused to move rearwardly into the member by a molten material and thereby provide an opening through which such a material can flow into the member.

28. A member for the use described, said member being hollow and having a front extremity which is constructed to provide an integral portion which will be caused to move rearwardly into the member by a molten material and thereby provide an opening through which such a material can flow into the member, said front extremity being provided with internal abutment means, and means for conditioning the material which is held between said abutment means and said integral portion.

29. A member for the use described, said member being hollow and having a front extremity which is constructed to provide an integral portion which will be caused to move rearwardly into the member by a molten material and thereby provide an opening through which such a material can flow into the member and, said integral portion being partially separated from said extremity whereby said portion is joined thereto by a connecting portion which will allow the integral portion to move into the member by such a material.

30. A subassembly for the use described comprising a pair of frusto-conical hollow members secured together in a telescoping relation to provide a pair of chambers, and said members being respectively provided with means responsive to molten material whereby to successively open said chambers to successively receive such a material.

31. In combination: a front hollow member for the use described and a rear hollow member telescopically connected to said front member to form front and rear chambers through which molten material may be caused to flow, at least one of said members having a front extremity provided with an integral portion which is hingedly connected thereto for inward movement by such a material to provide an opening to allow entry of such material for successive flow through said chambers.

32. The combination defined in claim 31, including means mounted in said front extremity for conditioning and mixing with such a material.

33. The combination defined in claim 31, in which the other member also has a front extremity provided with a substantially corresponding integral portion.

34. In combination: a mounting, a device connected to said mounting provided with a chamber and an entrance for receiving a sample of molten material for flow into the chamber, a hollow member secured in a protective relation to said entrance, and said hollow member having a front extremity provided with an integral pivotal portion which is responsive to such material whereby to permit entry of the material into the member.

35. The combination defined in claim 34, including a second similar hollow member connected to said first mentioned hollow member.

36. The combination defined in claim 34, in which said mounting, said device and said hollow member are assembled to constitute a composite unit for attachment to a front tubular extremity of an outer elongated housing and said hollow member is elongated and of a length appreciably greater than an axial dimension of said mounting.

37. In combination: an outer elongated housing having a front extremity, a device for receiving a sample of molten material secured to said extremity and provided with an entrance, a hollow member connected to said device in a protective relation to said entrance, and said member having a front extremity provided with an integral pivotal portion which when moved inwardly by such a material will provide an opening to allow entry of the material into the member for flow into said entrance.

38. The combination defined in claim 37, including means in said member adjacent to said pivotal portion for conditioning such a material prior to its flow into said entrance.

39. The combination defined in claim 37, including another hollow member connected to said first mentioned hollow member and provided with an integral pivotal portion for inward movement by such material to provide an opening for flow of the material successively from said member into said first-mentioned member.

40. A subassembly of a device for obtaining a sample of molten material, said subassembly comprising a mounting and a pair of sections, said mounting having a central hollow formation and an outer wall substantially surrounding said formation, each of said sections having a rear head and a front reduced channel portion, said head of one of said sections being provided with a center recess, a small cavity located in close proximity to one of said channel portions and with a small groove connecting said recess and said cavity, and means in said hollow formation for holding said sections assembled whereby said recesses, said cavities, said small grooves and channel portions respectively form a primary chamber, a secondary chamber, a passage communicatively connecting said chambers and a tubular formation for accommodating an inner extremity of a nonmetallic tube through which the material may be caused to flow into said chambers.

41. A subassembly of a device for obtaining a sample of molten material, said subassembly comprising a mounting and a pair of sections, said mounting having a central hollow formation, each of said sections having a rear head and front reduced channel portion, said head of at least one of said sections being provided with a center recess, a small cavity located in close proximity to one of said channel portions and with a small groove connecting said recess and said cavity, and means in said formation for holding said sections assembled whereby said recess, said cavity, said groove and channel portions respectively form a primary chamber, a secondary chamber, a passage communicatively connecting said chambers, a tubular formation for accommodating an inner extremity of a non-metallic tube through which such a material may be caused to flow into said chambers.

42. A subassembly of a device for obtaining a sample of molten material, said subassembly comprising a mounting and a pair of sections, said mounting having a central hollow formation, each of said sections having a rear head and a front reduced channel portion, at least one of said sections having a center recess in its head and a small cavity located in close proximity to its channel portion end with a small groove connecting said recess and said cavity, and means in said formation for holding said sections assembled whereby said recesses, said cavity, said small groove and channel portions respectively form a primary chamber, a secondary chamber, a passage communicatively connecting said chambers and a tubular formation for accommodating an inner extremity of a non-metallic tube through which the material may be caused to flow into said chambers.

43. A subassembly of a device for obtaining a sample of molten material, said subassembly comprising a mounting and a pair of mating sections, said mounting having a central hollow formation, at least one of said sections having a rear head provided with a center recess and a front reduced channel portion, said head also being provided with a small cavity located in close proximity to said channel portion and with a small groove connecting said recess and said cavity, and means in said formation for holding said sections assembled whereby said recess, said cavity, said groove and said channel portion in combination with the other section respectively form a primary chamber, a secondary chamber, a passage communicatively connecting said chambers and a tubular formation for accommodating an inner extremity of a non-metallic tube through which the material may be cuased to flow into said chambers.

* * * * *